US008921626B2

(12) United States Patent
Takahashi et al.

(10) Patent No.: US 8,921,626 B2
(45) Date of Patent: Dec. 30, 2014

(54) METHOD FOR OPERATING PLANT FOR PRODUCING MIXED-GAS HYDRATE

(75) Inventors: Masahiro Takahashi, Ichihara (JP); Nobuyasu Kanda, Ichihara (JP); Kenichi Sano, Ichihara (JP); Toru Iwasaki, Ichihara (JP)

(73) Assignee: Mitsui Engineering & Shipbuilding Co., Ltd., Tokyo (JP)

( * ) Notice: Subject to any disclaimer, the term of this patent is extended or adjusted under 35 U.S.C. 154(b) by 327 days.

(21) Appl. No.: 13/509,229

(22) PCT Filed: Nov. 9, 2010

(86) PCT No.: PCT/JP2010/069960

§ 371 (c)(1), (2), (4) Date: May 10, 2012

(87) PCT Pub. No.: WO2011/058980

PCT Pub. Date: May 19, 2011

(65) Prior Publication Data

US 2012/0232318 A1 Sep. 13, 2012

(30) Foreign Application Priority Data

Nov. 13, 2009 (JP) ................................ 2009-259469

(51) Int. Cl.
*C07C 9/00* (2006.01)
*C01B 3/32* (2006.01)
*C10L 3/06* (2006.01)
*C10L 3/10* (2006.01)
*F17C 11/00* (2006.01)

(52) U.S. Cl.
CPC . *C10L 3/06* (2013.01); *C10L 3/108* (2013.01); *F17C 11/007* (2013.01)
USPC ........................................... 585/15; 48/127.3

(58) Field of Classification Search
USPC ........................................................... 585/15
See application file for complete search history.

(56) References Cited

U.S. PATENT DOCUMENTS

| | | | | |
|---|---|---|---|---|
| 7,914,749 | B2 * | 3/2011 | Carstens et al. | 422/198 |
| 8,043,579 | B2 * | 10/2011 | Katoh et al. | 422/232 |
| 8,138,382 | B2 | 3/2012 | Kanda et al. | |
| 8,217,209 | B2 * | 7/2012 | Iwasaki et al. | 585/15 |
| 8,303,293 | B2 * | 11/2012 | Iwasaki et al. | 425/237 |
| 8,309,031 | B2 * | 11/2012 | Katoh et al. | 422/129 |
| 8,353,409 | B2 * | 1/2013 | Murayama et al. | 210/406 |
| 8,420,018 | B2 * | 4/2013 | Iwasaki et al. | 422/162 |

(Continued)

FOREIGN PATENT DOCUMENTS

| | | | |
|---|---|---|---|
| JP | 2003105362 | A | 4/2003 |
| JP | 2005320454 | A | 11/2005 |
| JP | 2008248190 | A | 10/2008 |
| JP | 2008248192 | A | 10/2008 |

*Primary Examiner* — Ellen McAvoy

(74) *Attorney, Agent, or Firm* — Westerman, Hattori, Daniels & Adrian, LLP

(57) ABSTRACT

The operation of a plant for producing a gas hydrate is stabilized by making the gas phase within a downstream step have the same equilibrium composition as that of the gas phase within a generation step. The gas phase within a mixed-gas hydrate generation step is circulated to the gas phase within a downstream step located downstream of the mixed-gas hydrate generation step, and the gas phase within each step is thereby made to have the same equilibrium composition as that of the gas phase within the generation step.

10 Claims, 3 Drawing Sheets

(56) References Cited

U.S. PATENT DOCUMENTS

| | | | | |
|---|---|---|---|---|
| 8,497,402 | B2 * | 7/2013 | Iwasaki et al. | 585/15 |
| 2005/0059846 | A1 * | 3/2005 | Kohda et al. | 585/15 |
| 2005/0107648 | A1 * | 5/2005 | Kimura et al. | 585/15 |
| 2010/0089834 | A1 | 4/2010 | Murayama et al. | |

* cited by examiner

METHOD FOR OPERATING PLANT FOR PRODUCING MIXED-GAS HYDRATE

CROSS-REFERENCE TO RELATED APPLICATIONS

The present patent application is a nationalization of International application No. PCT/JP2010/069960 filed Nov. 9, 2010 which is based on, and claims priority from, Japanese Application No. 2009-259469, filed Nov. 13, 2009, both of which are incorporated herein by reference in their entireties.

TECHNICAL FIELD

The present invention relates to a method for operating a plant for producing a mixed-gas hydrate by reaction between a mixed gas and water.

BACKGROUND ART

Heretofore, the following procedure has been known. Specifically, natural gas and water are reacted with each other at a temperature higher than the freezing point at a pressure higher than the atmospheric pressure to form a natural gas hydrate without freezing water. The natural gas hydrate thus formed is physically dewatered. Then, the water content of the natural gas hydrate is reduced by reacting natural gas with the residual water content contained in the natural gas hydrate during the physical dewatering step or after the dewatering to generate a natural gas hydrate. The resultant is cooled to a temperature lower than the freezing point, followed by depressurizing (see, for example, Patent Document 1).

However, in a case where the gas phase at the physical dewatering means, a transferring section, or the like has a natural gas composition in this production system, an additional gas hydrate may be generated from heavy components (ethane, propane, butane, and the like) contained in the composition. This may result in operation problems such as transferring failure in some cases.

To inhibit the occurrence of such operation problems, the gas phases in facilities downstream of the generation step have to be in an equilibrium state with hydrate and water, in other words, the gas phases have to have the same gas composition as that in the generation tank. As an invention analogous to this, for example, Patent Document 2 is known.

However, this invention requires a large-scale auxiliary facility for adjustment of a mixed gas supplied to a generation tank by dilution with a main component of the mixed gas, that is, requires a large-scale auxiliary facility including the control system. Further, the adjustment to the equilibrium composition is difficult under generation conditions, and there are still problems such as that a gas hydrate may be generated in the downstream facilities.

PRIOR ART DOCUMENT

Patent Documents

Patent Document 1: Japanese patent application Kokai publication No. 2003-105362

Patent Document 2: Japanese patent application Kokai publication No. 2008-248190

SUMMARY OF THE INVENTION

Problem to be Solved by the Invention

The present invention has been made to solve such problems. An object of the present invention is to simplify a plant without dilution facilities of a raw-material gas, and to provide a method for operating a plant for producing a mixed-gas hydrate, the method being capable of stabilizing the operation by making the gas phases within downstream steps have the same equilibrium composition as the gas phase of within a generation step.

Means for Solving the Problem

The present invention is characterized by including circulating a gas phase of a mixed-gas hydrate generation step to a gas phase within a downstream step located downstream of the mixed-gas hydrate generation step to thereby make the gas phase within each step have the same equilibrium composition as that of the gas phase within the generation step.

The present invention is characterized in that the downstream step is a dewatering step.

The present invention is characterized in that the downstream step includes a dewatering step, and a molding step, and a cooling step.

Effects of the Invention

In the present invention, the gas phase within the mixed-gas hydrate generation step is circulated to the gas phase within the downstream step located downstream of the mixed-gas hydrate generation step, and the gas phase within each step is thereby made to have the same equilibrium composition as that of the gas phase within the generation step. Accordingly, generation of an additional mixed-gas hydrate is suppressed in a physical dewatering facility and a transferring facility provided downstream of the generation step. This makes it possible in advance to eliminate likelihood of occurrence of operation problems such as clogging and malfunction of equipment attributed to the generation of a mixed-gas hydrate. Moreover, a diluting facility for a raw-material gas as in conventional inventions is no longer necessary, and simplification of the plant is achieved.

MODES FOR CARRYING OUT THE INVENTION

Hereinafter, embodiments of the present invention will be described by use of the drawings.

(1) Embodiment 1

Figure 1:
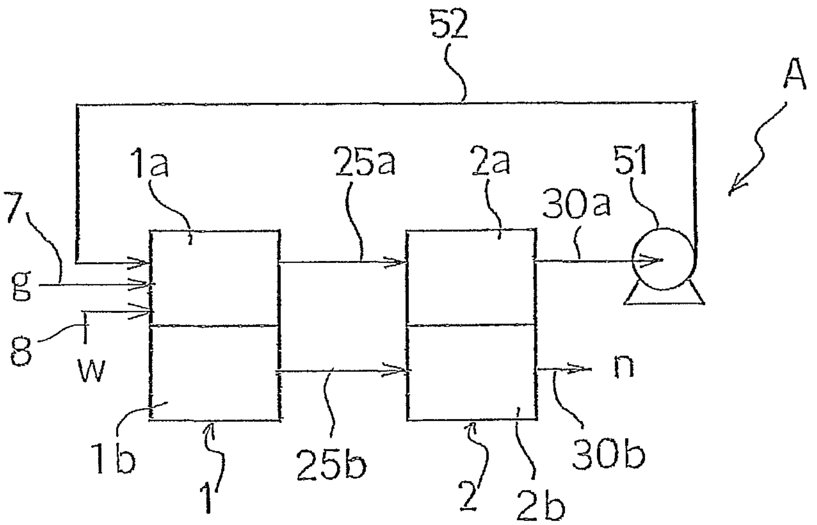
FIG. 1 is a block diagram for illustrating a basic process of a method for operating a plant for producing a mixed-gas hydrate according to the present invention.

As shown in FIG. 1, a basic plant A for producing a mixed-gas hydrate according to the present invention includes a gas hydrate generation tank 1 and a dewatering tower 2. A gas phase part 1*a* of the gas hydrate generation tank 1 communicates with a gas phase part 2*a* of the dewatering tower 2 through a first pipe 25*a*. The gas phase part 2*a* of the dewatering tower 2 communicates with the gas phase part 1*a* of the gas hydrate generation tank 1 through a second pipe 30*a*, a blower 51, and a circulation pipe 52.

Meanwhile, a solid-liquid part 1*b* of the gas hydrate generation tank 1 communicates with a solid-liquid part 2*b* of the dewatering tower 2 through a fifth pipe 25*b*. The solid-liquid part 2*b* of the dewatering tower 2 communicates with a facility for the subsequent process through a sixth pipe 30*b*. Moreover, the gas hydrate generation tank 1 includes a raw-material-gas supplying pipe 7 and a raw-material-water supplying pipe 8, and also includes a stirrer (unillustrated) for stirring the solid-liquid phase.

Next, a method for operating the plant for producing a mixed-gas hydrate will be described.

A mixed gas, for example, natural gas g, supplied into the gas hydrate generation tank 1 through the raw-material-gas supplying pipe 7 is reacted with water w supplied through the raw-material-water supplying pipe 8 to thereby form a natural gas hydrate. The natural gas hydrate in the gas hydrate generation tank 1 is supplied to the dewatering tower 2 together with water w for dewatering. The dewatered natural gas hydrate h is drawn out to the facility for the subsequent process through the sixth pipe 30*b*.

Meanwhile, driving the blower 51 forces an unreacted gas in the gas phase part 1*a* of the gas hydrate generation tank 1 to circulate from the gas phase part 1*a* of the gas hydrate generation tank 1 through the first pipe 25*a*, the gas phase part 2*a* of the dewatering tower 2, the fourth pipe 30*a*, the blower 51, and the circulation pipe 52 to the gas phase part 1*a* of the gas hydrate generation tank 1.

Thus, the gas phase within the gas phase part 2*a* of the dewatering tower 2 has the same equilibrium composition as the gas phase (unreacted gas) within the gas phase part 1*a* of the gas hydrate generation tank 1. Accordingly, generation of an additional gas hydrate is suppressed in the downstream facilities such as the dewatering tower 2. This suppresses operation problems such as clogging and malfunction of the equipment.

Note that the same effects can also be obtained by connecting the raw-material-gas supplying pipe 7 and the circulation pipe 52 together to mix the natural gas g supplied through the raw-material-gas supplying pipe 7 with the unreacted gas circulated through the circulation pipe 52.

(2) Embodiment 2

Figure 2:
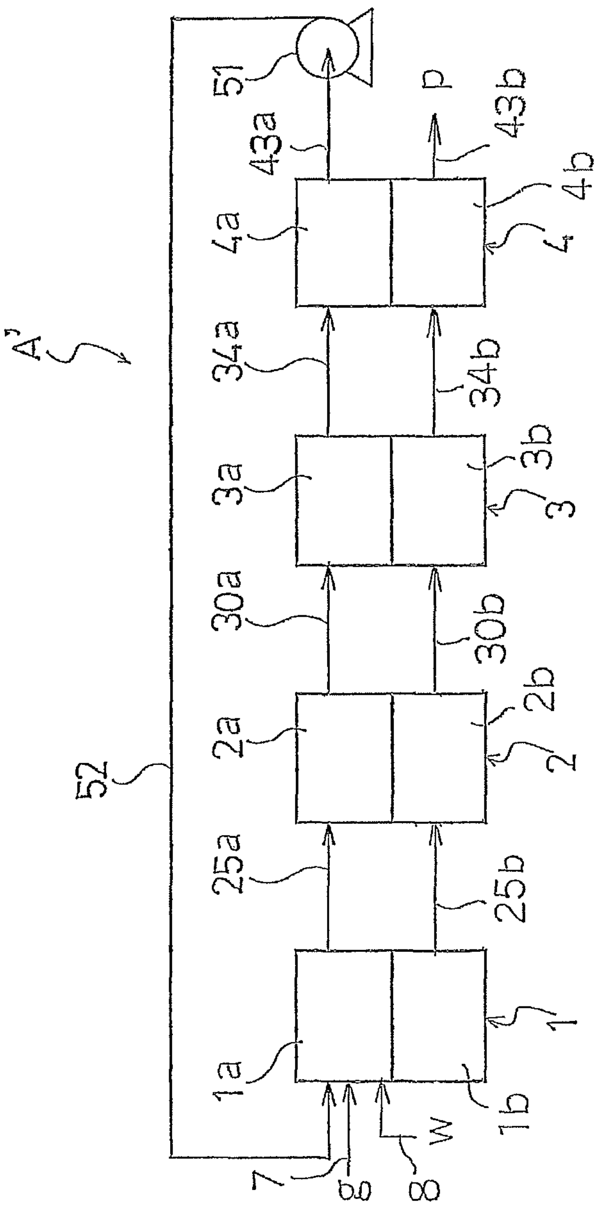
FIG. 2 is a block diagram for illustrating a process for actual application of the method for operating a plant for producing a mixed-gas hydrate according to the present invention.

As shown in FIG. 2, a plant A' for producing a mixed-gas hydrate according to the present invention includes a gas hydrate generation tank 1, a dewatering tower 2, a pelletizer 3, and a pellet cooling tank 4. A gas phase part 1*a* of the gas hydrate generation tank 1 communicates with a gas phase part 2*a* of the dewatering tower 2 through a first pipe 25*a*. The gas phase part 2*a* of the dewatering tower 2 communicates with a gas phase part 3*a* of the pelletizer 3 through a second pipe 30*a*. The gas phase part 3*a* of the pelletizer 3 communicates with a gas phase part 4*a* of the pellet cooling tank 4 through a third pipe 34*a*. The gas phase part 4*a* of the pellet cooling tank 4 communicates with the gas phase part 1*a* of the gas hydrate generation tank 1 through a fourth pipe 43*a*, a blower 51, and a circulation pipe 52.

Meanwhile, a solid-liquid part 1*b* of the gas hydrate generation tank 1 communicates with a solid-liquid part 2*b* of the dewatering tower 2 through a fifth pipe 25*b*. The solid-liquid part 2*b* of the dewatering tower 2 communicates with a solid-liquid part 3*b* of the pelletizer 3 through a sixth pipe 30*b*. The solid-liquid part 3*b* of the pelletizer 3 communicates with a solid-liquid part 4*b* of the pellet cooling tank 4 through a seventh pipe 34*b*. The solid-liquid part 4*b* of the pellet cooling tank 4 communicates with a facility for the subsequent process through an eighth pipe 43*b*.

Moreover, the gas hydrate generation tank 1 includes a raw-material-gas supplying pipe 7 and a raw-material-water supplying pipe 8, and also includes a stirrer (unillustrated) for stirring the solid-liquid phase.

Next, a method for operating the plant for producing a mixed-gas hydrate will be described.

A mixed gas, for example, natural gas g, supplied into the gas hydrate generation tank 1 through the raw-material-gas supplying pipe 7 is reacted with water w supplied through the raw-material-water supplying pipe 8 to thereby form a natural gas hydrate. The natural gas hydrate in the gas hydrate generation tank is supplied to the dewatering tower 2 together with water w for dewatering. The dewatered natural gas hydrate is supplied to the pelletizer 3 through the sixth pipe 30*b*, and molded into pellets in predetermined shape and size. The pellets are supplied to the pellet cooling tank 4 through the seventh pipe 34*b*, and cooled to a predetermined temperature. The pellets thus cooled are drawn out to the facility for the subsequent process through the eighth pipe 43*b*.

Meanwhile, driving the blower 51 forces an unreacted gas in the gas phase part 1*a* of the gas hydrate generation tank 1 to circulate from the gas phase part 1*a* of the gas hydrate generation tank 1 through the first pipe 25*a*, the gas phase part 2*a* of the dewatering tower 2, the second pipe 30*a*, the gas phase part 3*a* of the pelletizer 3, the third pipe 34*a*, the gas phase part 4*a* of the pellet cooling tank 4, the fourth pipe 43*a*, the blower 51, and the circulation pipe 52 to the gas phase part 1*a* of the gas hydrate generation tank 1.

Thus, the gas phases within the gas phase part 2*a* of the dewatering tower 2, the gas phase part 3*a* of the pelletizer 3, and the gas phase part 4*a* of the pellet cooling tank 4 have the same equilibrium composition as the gas phase (unreacted gas) within the gas phase part 1*a* of the gas hydrate generation tank 1. Accordingly, generation of an additional gas hydrate is suppressed in the downstream facilities such as the dewatering tower 2, the pelletizer 3, and the pellet cooling tank 4. This suppresses operation problems such as clogging and malfunction of the equipment.

Note that the same effects can also be obtained by connecting the raw-material-gas supplying pipe 7 and the circulation pipe 52 together to premix the natural gas g supplied through the raw-material-gas supplying pipe 7 with the unreacted gas circulated through the circulation pipe 52.

(3) Embodiment 3

Figure 3:
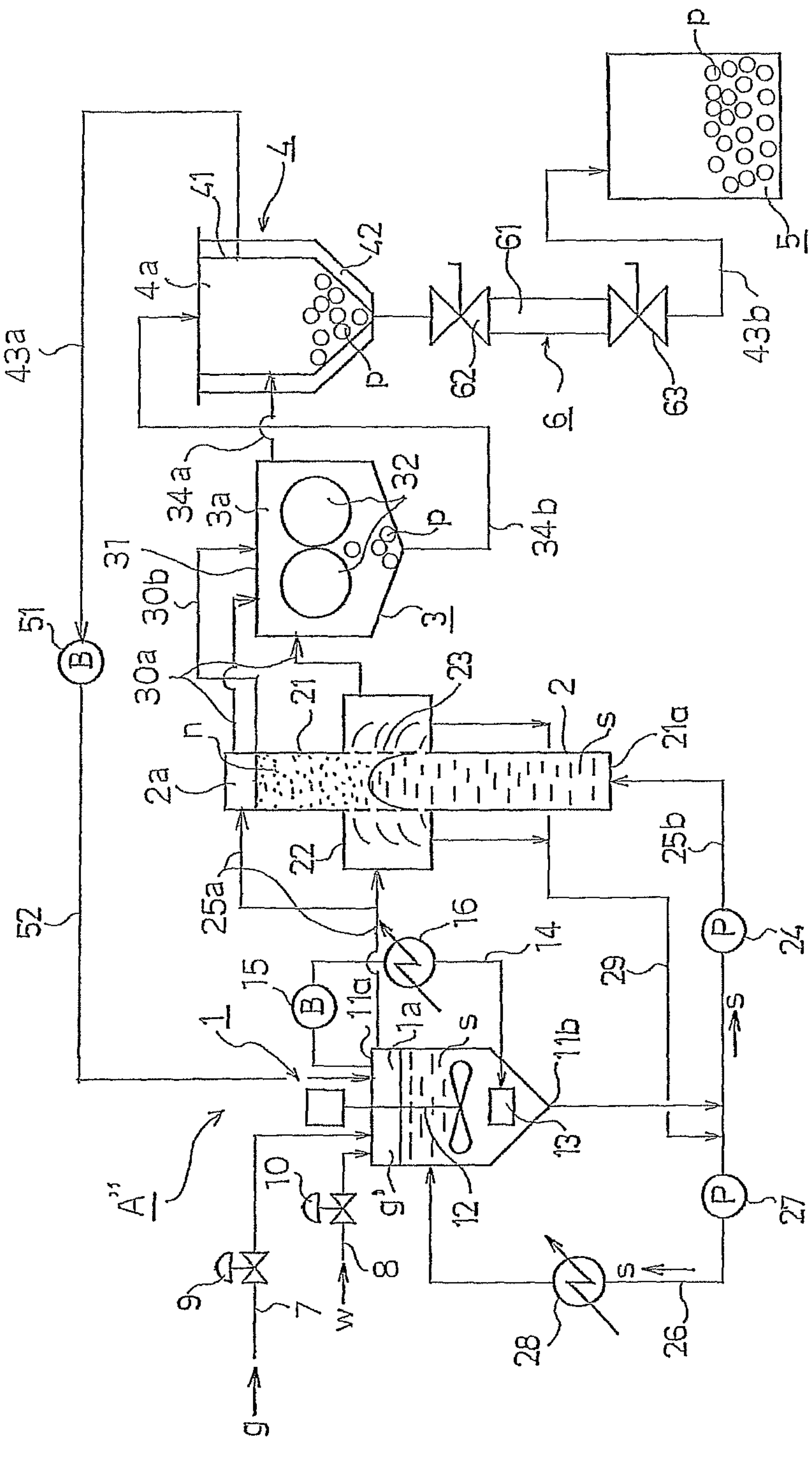
FIG. 3 is a schematic configuration diagram of a plant for producing a mixed-gas hydrate according to the present invention.

As shown in FIG. 3, a plant A" for producing a mixed-gas hydrate of the present invention includes a gas hydrate generation tank 1, a dewatering tower 2, a pelletizer 3, a pellet cooling tank 4, a pellet storage tank 5, and a depressurizing device 6.

The gas hydrate generation tank 1 includes a stirrer 12, and also includes a gas-jetting nozzle 13 below the stirrer 12. The gas hydrate generation tank 1 includes a raw-material-gas supplying pipe 7 and a raw-material-water supplying pipe 8 at a top portion 11*a* thereof. The raw-material-gas supplying pipe 7 includes a flow-amount adjusting valve 9, and the raw-material-water supplying pipe 8 includes a valve 10.

The gas hydrate generation tank 1 includes a gas-circulation path 14 through which the top portion 11*a* communicates with the gas-jetting nozzle 13. An unreacted gas g' in a gas phase part 1*a* is supplied to the gas-jetting nozzle 13 by a first blower 15, and cooled to a predetermined temperature by a first cooler 16. The gas phase part 1*a* of the gas hydrate generation tank 1 communicates with a gas phase part 2*a* of the dewatering tower 2 through a first pipe 25*a*.

Meanwhile, a bottom portion 11*b* of the gas hydrate generation tank 1 communicates with a bottom portion 21*a* of the dewatering tower 2 through a fifth pipe (slurry supplying pipe) 25*b* including a slurry pump 24. A slurry circulation path 26 branched from the slurry supplying pipe 25*b* is connected to a side surface of the gas hydrate generation tank 1. The slurry circulation path 26 includes a second slurry pump 27 and a second cooler 28, and cools a slurry s passing through the slurry circulation path 26.

The dewatering tower 2 includes a vertical cylindrical tower body 21, a hollow drainage part 22 provided concentrically to and outside the tower body 21, and a screen 23 provided in the tower body portion facing the drainage part 22. The drainage part 22 communicates with the slurry circulation path 26 through a drainage pipe 29. The dewatering tower 2 supplies a dewatered gas hydrate n to the pelletizer 3 through a sixth pipe (screw feeder) 30*b*. Moreover, the gas phase part 2*a* of the dewatering tower 2 and a gas phase part 2*a* of the drainage part 22 communicate with a gas phase part 3*a* of the pelletizer 3 through second pipes 30*a*.

The pelletizer 3 is a high-pressure pelletizer in which a pair of briquetting rolls 32, 32 are provided in a pressure-tolerable container 31. The pelletizer 3 forms pellets p in a predetermined shape (for example, lens shape, almond shape, pillow shape, or the like) from a powdery gas hydrate. Moreover, the gas phase part 3*a* of the pelletizer 3 communicates with a gas phase part 4*a* of the pellet cooling tank 4 through a third pipe 34*a*. Further, a lower end portion of the pelletizer 3 is connected to an upper end portion of the pellet cooling tank 4 through a seventh pipe (pellet discharging duct) 34*b*.

The pellet cooling tank 4 includes a hopper-shaped hollow container 41 and a cooling jacket 42 provided outside the hollow container 41. The cooling jacket 42 cools the pellets p in the hollow container 41. Moreover, the pellet cooling tank 4 is connected to the top portion 11*a* of the gas hydrate generation tank 1 through a fourth pipe 43*a* and a circulation pipe 52 including a second blower 51.

The depressurizing device 6 is provided in a middle portion of an eighth pipe (duct) 43*b* through which a lower end portion of the pellet cooling tank 4 communicates with an upper end portion of the pellet storage tank 5. The depressurizing device 6 includes an upper valve 62 on an upper portion of a cylindrical container 61 and a lower valve 63 on a lower portion of the cylindrical container 61.

Next, a method for operating the plant for producing a mixed-gas hydrate will be described.

First, water w in the gas hydrate generation tank 1 is cooled to a predetermined temperature (for example, 3° C.) by driving the second slurry pump 27 and the second cooler 28 provided in the slurry circulation path 26.

Then, while a mixed gas, for example, natural gas g, at a predetermined pressure (for example, 5 MPa) is being supplied from the raw-material-gas supplying pipe 7 to the gas hydrate generation tank 1, the unreacted gas g' in the gas phase part 1*a* of the gas hydrate generation tank 1 is supplied to the gas-jetting nozzle 13 by driving the first blower 15 and the first cooler 16 provided in the gas-circulation path 14.

The natural gas g supplied to the gas-jetting nozzle 13 is jetted as numerous fine bubbles into the water w, and then stirred with the stirrer 12. Accordingly, the natural gas g and the water w are subjected to hydration reaction to form a natural gas hydrate.

The composition of the natural gas is: 86.88% of methane, 5.20% of ethane, 1.86% of propane, 0.42% of i-butane, 0.47% of n-butane, 0.15% of i-pentane, of 0.08% of n-pentane, 1% of carbon dioxide, and so forth. However, since the heavy parts such as ethane and propane are likely to react with water, the gas phase within the gas phase part 1*a* of the gas hydrate generation tank 1 is rich in methane.

The natural gas hydrate with the water w forms a slurry s, which is supplied to the bottom portion 21*a* of the dewatering tower 2 by the slurry pump 24. The gas hydrate n dewatered by the dewatering tower 2 is supplied to the pelletizer 3 from an upper portion of the dewatering tower 2 through the sixth pipe (screw feeder) 30*b*, and processed into the pellets p in predetermined shape and size.

The pellets p molded by the pelletizer 3 are supplied to the pellet cooling tank 4 through the seventh pipe (pellet discharging duct) 34*b*, and cooled to a predetermined temperature (for example, −20° C.). The pellets p cooled by the pellet cooling tank 4 are depressurized by the depressurizing device 6 to a predetermined pressure (for example, a pressure slightly higher than the atmospheric pressure), and then stored in the pellet storage tank 5.

Meanwhile, since the second blower 51 is driven, the unreacted gas g' in the gas phase part 1*a* of the gas hydrate generation tank 1 is forced to return to the gas phase part 1*a* of the gas hydrate generation tank 1 through the first pipe 25*a*, the gas phase part 2*a* of the dewatering tower 2, the second pipe 30*a*, the gas phase part 3*a* of the pelletizer 3, the third pipe 34*a*, the gas phase part 4*a* of the pellet cooling tank 4, the fourth pipe 43*a*, and the circulation pipe 52.

Thus, the gas phases within the gas phase part 2*a* of the dewatering tower 2, the gas phase part 3*a* of the pelletizer 3, and the gas phase part 4*a* of the pellet cooling tank 4 have the same equilibrium composition as the gas phase (unreacted gas g') within the gas phase part 1*a* of the gas hydrate generation tank 1. Accordingly, generation of an additional gas hydrate is suppressed in the downstream facilities such as the dewatering tower 2, the pelletizer 3, and the pellet cooling tank 4, or the first to the fourth pipes 25*a*, 30*a*, 34*a*, 43*a*. This suppresses operation problems such as clogging and malfunction of the equipment.

Note that the same effects can also be obtained by connecting the raw-material-gas supplying pipe 7 and the circulation pipe 52 together to premix the natural gas g supplied through the raw-material-gas supplying pipe 7 with the unreacted gas' returned through the circulation pipe 52.

EXPLANATION OF REFERENCE NUMERALS

1 gas hydrate generation tank
2 dewatering tower
3 pelletizer
4 pellet cooling tank

What is claimed is:

1. A method for operating a plant for producing a mixed-gas hydrate, wherein the plant includes a gas hydrate generation tank having a first gas phase part, and processing equipment downstream of the gas hydrate generation tank, the processing equipment having a second gas phase part in fluid communication with the first gas phase part, the method comprising the steps of:

generating a mixed gas hydrate in the gas hydrate generation tank, the first gas phase part having a gas phase therein during the generating step;

processing the mixed-gas hydrate in the processing equipment downstream of the gas hydrate generation, the second gas phase part having a gas phase therein during the processing step; and forcibly circulating the gas phase from the first gas phase part to the second gas phase part, and then back to the first gas phase part, during the generating and processing steps, to make the gas phase within the second gas phase part during the processing step have the same equilibrium composition as that of the gas phase within the first gas phase part during the generating step.

2. The method for operating a plant for producing a mixed-gas hydrate according to claim 1, wherein the processing step is a dewatering step.

3. The method for operating a plant for producing a mixed-gas hydrate according to claim 1, wherein the processing step includes dewatering the mixed-gas hydrate, molding the dewatered mixed-gas hydrate into pellets, and cooling the pellets.

4. The method for operating a plant for producing a mixed-gas hydrate according to claim 3, wherein the second gas phase part is used in the dewatering step, the molding step is carried out using a third gas phase part in communication with the second gas phase part, the cooling step is carried out using a fourth gas phase part in communication with the third gas phase part, and wherein in the circulating step, the gas phase is forcibly circulated from the second gas phase part to the third gas phase part, from the third gas phase part to the fourth gas phase part, and from the fourth gas phase part back to the first gas phase part during the generating and processing steps, to make the gas phase within the second, third, and fourth gas phase parts during the processing step have the same equilibrium composition as that of the gas phase within the first gas phase part during the generating step.

5. The method for operating a plant for producing a mixed-gas hydrate according to claim 1, wherein in the circulating step, the gas phase is forcibly circulated from the second gas phase part directly back to the first gas phase part.

6. The method for operating a plant for producing a mixed-gas hydrate according to claim 2, wherein in the circulating step, the gas phase is forcibly circulated from the second gas phase part directly back to the first gas phase part.

7. The method for operating a plant for producing a mixed-gas hydrate according to claim 1, wherein in the circulating step, the gas phase is forcibly circulated from the second gas phase part indirectly back to the first gas phase part.

8. The method for operating a plant for producing a mixed-gas hydrate according to claim 3, wherein in the circulating step, the gas phase is forcibly circulated from the second gas phase part indirectly back to the first gas phase part.

9. The method for operating a plant for producing a mixed-gas hydrate according to claim 1, wherein in the circulating step, the gas phase is forcibly circulated using a blower.

10. The method for operating a plant for producing a mixed-gas hydrate according to claim 1, wherein in the circulating step, the gas phase forcibly circulated from the first gas phase part to the second gas phase is unreacted gas.

* * * * *